United States Patent [19]

Rubin et al.

[11] Patent Number: 4,815,456

[45] Date of Patent: Mar. 28, 1989

[54] HYGIENIC DEVICE

[76] Inventors: Harold Rubin, 23313 Fernwood Dr., Beachwood, Ohio 44122; Leonard J. Cosentino, 14 Forrest Dr., Chagrin Falls, Ohio 44022

[21] Appl. No.: 75,551

[22] Filed: Jul. 20, 1987

[51] Int. Cl.⁴ ................................................ A61F 8/56
[52] U.S. Cl. ..................... 128/859; 604/352; 604/353; 128/206.12; 128/206.13; 128/206.14; 128/830; 128/844
[58] Field of Search ................. 128/163, 169, 201.18, 128/201.19, 201.22, 201.23, 201.24, 201.25, 205.25, 205.26, 205.27, 206.12, 206.13, 206.14, 201.14, 201.15, 201.26, 206.21, 206.28, 206.23, 206.24, 136, 132 R; 604/353

[56] References Cited

U.S. PATENT DOCUMENTS

| | | | |
|---|---|---|---|
| 1,986,988 | 1/1935 | Treadwell | 128/136 |
| 2,082,153 | 6/1937 | Dopyera | 128/163 |
| 2,406,600 | 8/1946 | Forestiere | 128/132 R |
| 2,494,406 | 1/1950 | Reitano | 128/206.13 |
| 2,667,869 | 2/1954 | D'Elia | 128/206.13 |
| 2,928,388 | 3/1960 | Jaroslaw | 128/206.14 |
| 3,315,674 | 4/1967 | Bloom et al. | 128/206.12 |
| 3,536,066 | 10/1970 | Ludwig | 604/353 |
| 3,677,225 | 7/1972 | Czirely | 604/352 |
| 4,195,629 | 4/1980 | Halford | 128/206.13 |

*Primary Examiner*—Robert A. Hafer
*Assistant Examiner*—Charles H. Sam
*Attorney, Agent, or Firm*—Krass & Young

[57] ABSTRACT

A device is disclosed for providing reduced opportunity for germs, viruses and other substances from entering the human mouth under various circumstannces. The device comprises a planar latex membrane adapted to be worn over the mouth and attached to the ears, and having a hollow, generally conical or cylindrical protuberant extension of the membrane deviating from the planar cofiguration at a central location.

4 Claims, 1 Drawing Sheet

HYGIENIC DEVICE

BACKGROUND OF THE INVENTION

1. Field of the Invention

This invention relates generally to the field of human hygiene, and more particularly relates to a membranous latex device for use over a human mouth.

2. Description of the Prior Art

In various circumstances it is desired to provide some margin of isolation of the human mouth and/or tongue from external objects. Included in these circumstances are various practices as may be engaged in sexually by a husband and wife. And with the grave recent concern over certain communicable diseases transmitted during intimacy, such as, for example AIDS (acquired immune defficiency syndrome), the need for such an isolating device is becoming even more important.

Until this present invention, there has never been an acceptable device to provide such a margin of isolation.

SUMMARY OF THE INVENTION

The present invention provides such a device, and comprises: a thin generally planar pliable membrane material having two end portions; straps at each of the end portions; a hollow protuberance centrally located between the end portions comprising a continuous deviated surface extension of the membrane material.

BRIEF DESCRIPTION OF THE DRAWINGS

The invention can be more readily understood by reference to the accompanying DRAWING FIGURES, in which.

DESCRIPTION OF THE PREFERRED EMBODIMENT

Figure 1:
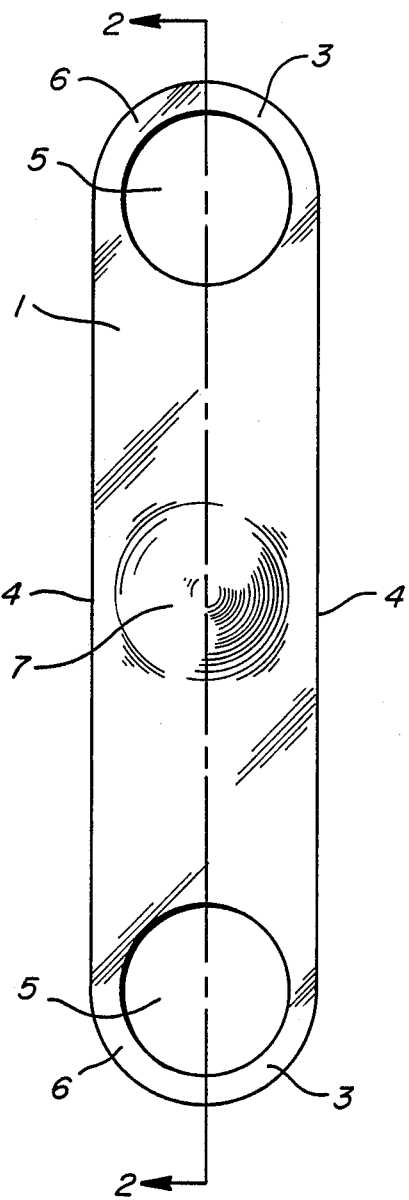
FIG. 1 depicts a top view of a hygienic device for use over the human mouth.
Figure 2:
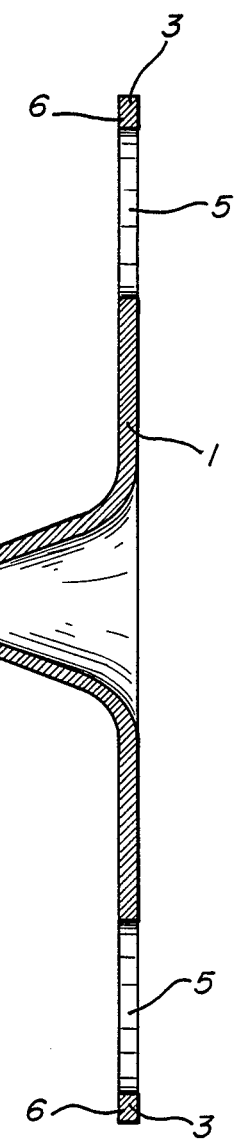
FIG. 2 depicts a crossectional view of the device for FIG. 1 taken on the plane indicated by the phantom lines 2—2 in FIG. 1.

The device comprises a thin, generally flat planar pliable membrane 1 elongated in a first planar direction between two rounded ends 3, and having two side edges 4 defining a second planar direction transverse to the first.

Proximate each rounded end 3 is a generally circular hole 5 in the fabric of the membrane 1. The holes 5 form continuous marginal straps 6 at each of the rounded ends 3 as continuous extensions of the membrane material. The holes 5 in the ends 3 are to accomodate human ears such that the device can be worn as a mask over the mouth area and snugly retained there by the straps 6 stretched over and positioned around the ears. Thus, the openings 5 are large enough to accomodate at least the partial passage therethrough of human ears.

A generally conical hollow protuberance 7 is formed in the membrane 1 centrally between the two ends 3 and between the two side edges 4. The protuberance is made as a continuous surface extension of membrane material but which deviates from the general planar configuration thereof. The protuberance 7 is adapted to accomodate a human tongue for whatever purpose the user might desire, and is thus made of an appropriate size.

The various dimensions of the device will depend on the size of the particular person it may be intended for. A snug fit around the ears and across the mouth is preferred, and the selection of the particular dimensions to accomplish this can readily be determined by a person of ordinary skill in the art. In order to provide the snug fit, the dimension of the device in the first planar direction should be less than the average topological distance from the back of the average human ears around the front of the face across the mouth area. Thus the device would be stretched in use to provide the snug fit. In general, the device can variably have dimensions in the range of 8 to 15 inches in the planar direction of elongation between the ends 3, and 2 to 5 inches in the transverse planar direction between its side edges 4. The thickness of the membrane, including the protuberance can be in a wide range, but generally as thin as possible to give maximum pliancy without tearing or rupturing in use. An acceptable range has been found to be 0.003 to 0.020 inches. Depending on the nature of the material used for the membrane, thicknesses outside of this range may also be acceptable. The protuberance 7 can have a diametral base dimension in the range of ¼ inch to 3 inches and a height in the range of ½ inch to 4 inches.

Latex has been found to be a suitable material owing to its pliable, resilient characteristics and its ability to be formed into a thin planar form.

Having described the invention, we claim:

1. A hygienic barrier device comprising:

a continuous, seamless, elastomeric membrane of a uniform thickness in a range of between 0.003 to 0.020 inches and of a generally flat, rectangular shape configured to include a generally conical protuberance approximately 1 to 3 inches in height and approximately 1 to 2 inches in diameter at the base disposed in the approximate center thereof and adapted to receive a human tongue therein, said membrane provided with means defining an opening proximate each of the ends thereof, each of said openings adapted to permit passage of a human ear therethrough, whereby said device is adapted to be fixedly retained upon a human face and cover the lips, mouth and tongue thereof, so as to form a continuous barrier to disease causing agents.

2. The hygienic barrier device of the claim 1 wherein the elastomeric membrane is comprised of latex.

3. The hygienic barrier device of claim 1 wherein the rectangular membrane has a length in a range of between 8 and 15 inches and a width in a range of between 2 and 5 inches.

4. A hygienic barrier device comprising:

a continuous, seamless, elastomeric membrane of latex of a uniform thickness in a range of between 0.003 and 0.020 inches and a generally flat rectangular shape having a length in a range of between 8 and 15 and a width in a range of between 2 and 5 inches, said member being configured to include a generally conical protuberance disposed in the approximate center thereof and adapted to receive a human tongue therein, said protuberance having a base diameter in a range of approximately 1 inch and a height in a range of approximately 2 inches, said membrane provided with means defining an opening proximate each of the ends thereof, each of said openings adapted to permit passage of a human ear therethrough, whereby said device is adapted to be fixedly retained upon a human face and cover the lips, mouth and tongue thereof, so as to form a continuous barrier to disease causing agents.

* * * * *